United States Patent [19]

Frank

[11] 4,313,431
[45] Feb. 2, 1982

[54] ENDOSCOPIC APPARATUS WITH A LASER LIGHT CONDUCTOR

[75] Inventor: Frank Frank, Munich, Fed. Rep. of Germany

[73] Assignee: Messerschmitt-Boelkow-Blohm Gesellschaft mit beschraenkter Haftung, Munich, Fed. Rep. of Germany

[21] Appl. No.: 97,200

[22] Filed: Nov. 26, 1979

[30] Foreign Application Priority Data

Dec. 6, 1978 [DE] Fed. Rep. of Germany ....... 2852653
Nov. 8, 1979 [DE] Fed. Rep. of Germany ....... 2945080

[51] Int. Cl.³ .......................... A61B 1/06; A61B 1/12
[52] U.S. Cl. ..................................... 128/7; 128/303.1
[58] Field of Search ............... 128/303.1, 303.15, 4, 128/6, 7, 328, DIG. 9, 8

[56] References Cited

U.S. PATENT DOCUMENTS

| | | | |
|---|---|---|---|
| 3,799,151 | 3/1974 | Fukaumi et al. | 128/6 |
| 3,835,842 | 9/1974 | Iglesias | 128/7 |
| 4,211,229 | 7/1980 | Wurster | 128/303.1 |

OTHER PUBLICATIONS

"Fortschritte der Medizin" No. 1, vol. 95, pp. 3-7, Staehler et al. (Jan. 1977).
"Aktuelle Urologie" vol. 9, pp. 271-274, Hohenfellner et al. (Sep. 1978).

*Primary Examiner*—Michael H. Thaler
*Attorney, Agent, or Firm*—W. G. Fasse; D. F. Gould

[57] ABSTRACT

The present endoscopic apparatus with a laser light conductor is used for irradiating bladder tumors in man with a laser light beam. For this purpose a jacketed light conducting fiber is arranged in parallel to an optical viewing device. A rigid bushing is secured to the output end of the light conducting fiber. The bushing includes a hinging member connected to a push rod or cable pull for remote manipulation of the output end of the light conduct ng fiber. Preferably, the light conducting fiber is axially shiftable in its jacket. For this purpose a shifting device, located at the input or operating end of the apparatus is operatively connected to the light conducting fiber.

10 Claims, 6 Drawing Figures

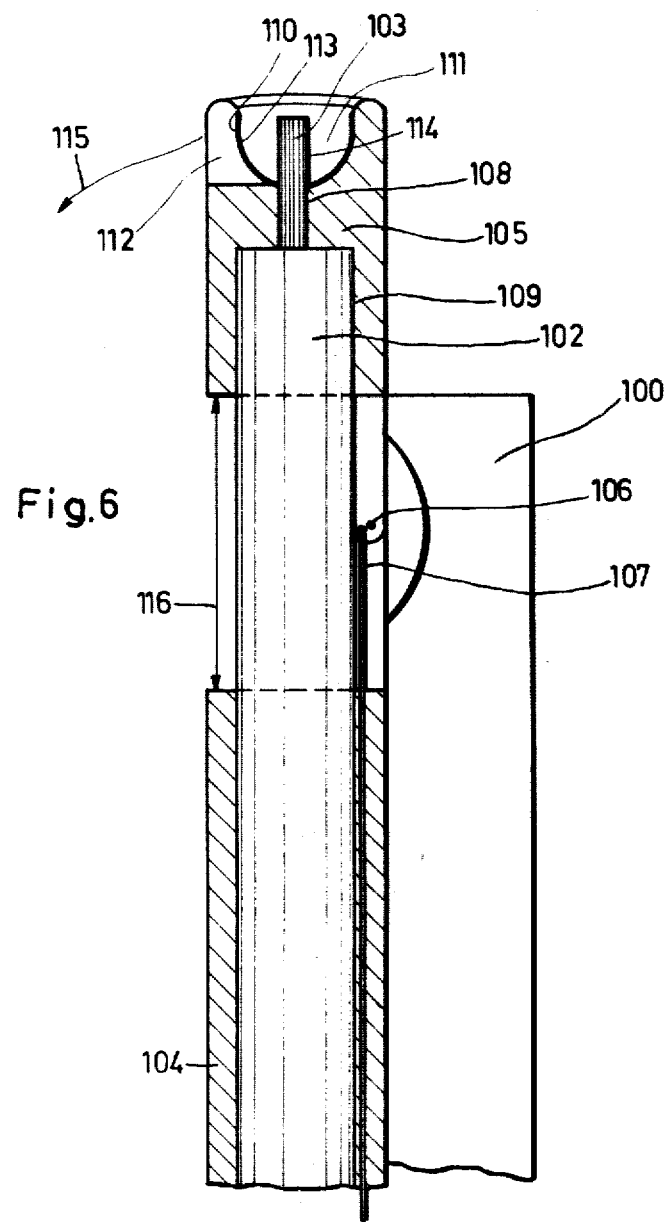

ENDOSCOPIC APPARATUS WITH A LASER LIGHT CONDUCTOR

BACKGROUND OF THE INVENTION

The present invention relates to an endoscopic apparatus with a laser light conductor, particularly for the irradiation of bladder tumors in man. The present apparatus is adapted to cause the complete necrosis of the tumor without the need for a perforation of the bladder wall.

Prior art devices of the above mentioned type are described in the periodicals: "Fortschritte der Medizin", Number 1, Volume 95, pages 3 to 7; and in "aktuelle urologie", Volume 9, (1978), pages 271 to 274. In the prior art devices a conventional cystoscope is combined with a light conductor. Such devices have been used successfully for the above mentioned treatment of bladder tumors. However, it has been found that substantial difficulties have been encountered in obtaining a precisely defined laser light output power of a sufficient size available at the output end of the light conductor. Further, it is difficult to steer or train the light beam substantially without loss of power onto a tumor to be treated at any desired location on the inner surface of the bladder wall.

For the last mentioned purposes deflecting mirrors have been used. However, such mirrors have the disadvantage that they are heated up by absorbing the laser radiation. Such heat-up has resulted in the destruction of the deflecting mirror when higher laser energies have been used which are suitable for the tumor treatment.

It has also been tried heretofore to deflect the laser beam by means of a glass or quartz prism rather than by means of a mirror. However, in such an arrangment the light conductor output is covered by a glass or quartz prism or with a window for a so-called "prograde" irradiation. The glass or quartz window as well as the movable prism both require special auxiliary means for keeping these components clean just directly prior to the laser irradiation, for example by means of a water and air rinsing. Even small contaminations cause an instantaneous burn-in on the mentioned components and thus quite frequently a destruction of the apparatus.

It is also necessary in devices without prism or window to keep the output end of the light conductor such as a light conducting fiber clean during its use inside the bladder because the liquid in the bladder may soil the output end, whereby the capability of the light conductor to function properly is impaired and the laser irradiation is correspondingly impaired. The endoscopic apparatus then has to be removed from the urinary tract for a cleaning and thereafter it must be introduced again which should be avoided since the procedure may be rather painful.

OBJECTS OF THE INVENTION

In view of the above it is the aim of the invention to achieve the following objects singly or in combination:

to construct a light conductor of small diameter, for example, a quartz glass fiber having a diameter of 0.4 to 0.6 mm and a small bending radius, so that it will be suitable for use in endoscopic applications;

to assure that the light output end of such a light conductor or light conducting fiber will provide a relatively high output power up to about 150 Watts of laser light power;

to make sure that the light conductor and the means for deflecting the laser light beam do not interfere in any way whatsoever with the proper functioning and use of the endoscopic apparatus;

to provide means which will enable the cleaning of the light conductor output end while it is inserted in an operational position inside the bladder;

to avoid the repeated introduction and removal of the endoscope into the urinary tract during a required treatment; and to improve the functional capability of the light conductor.

SUMMARY OF THE INVENTION

According to the invention there is provided an endoscopic apparatus with a laser light conductor to the output end of which there is attached a rigid sleeve or bushing which is provided with a hinging means extending substantially perpendicularly to the longitudinal axis of the light conductor. The hinging means are movable by a push rod or a rope or cable pull for bending the output end of the light conductor.

According to the invention there is further provided an endoscopic apparatus in which the light conductor fiber is guided in the above mentioned sleeve for a longitudinal shifting or displacement. Additionally, the operating end of the endoscopic apparatus is provided with a device for the longitudinal displacement of the light conductor fiber. In a preferred embodiment of the invention the light conductor fiber and its jacket are secured in a glide bearing which is movable in a housing against the force of a spring, whereby the movement of the glide bearing enables the adjustment or positioning of the light conductor fiber output end into a position suitable for the tumor treatment or irradiation.

BRIEF FIGURE DESCRIPTION

In order that the invention may be clearly understood, it will now be described, by way of example, with reference to the accompanying drawings, wherein:

FIG. 6 is a longitudinal sectional view through the upper end of the light conductor, whereby the endoscopic viewing means are only shown schematically.

Figure 1:
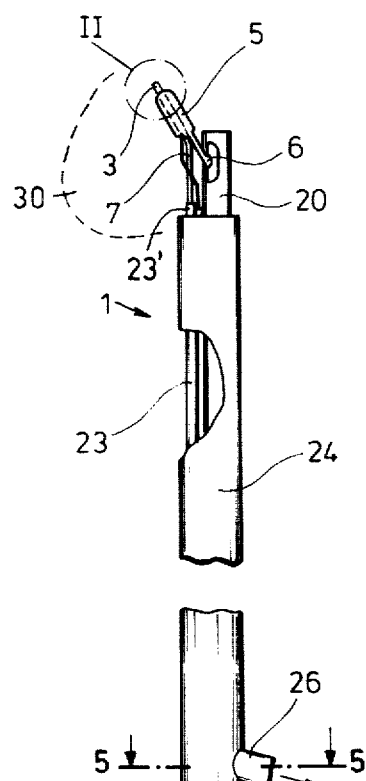
FIG. 1 is an elevational view of an embodiment of an apparatus according to the invention for the endoscopic laser irradiation of human bladder tumors.

DETAILED DESCRIPTION OF PREFERRED EXAMPLE EMBODIMENTS AND OF THE BEST MODE OF THE INVENTION

Referring first to FIG. 6, a conventional endoscopic viewing device 100 is arranged in parallel to a light conductor fiber 103 provided with a jacket 102. A sleeve, preferably a rigid sleeve 104 holds the fiber 103 with its jacket 102 and is preferably rigidly secured to the housing of the endoscopic viewing device 100.

The light output end 114 of the light conductor fiber 103 is free of the jacket 102 and extends through a bore 108 in a heat absorbing metal sleeve or bushing 105. The bushing is provided with a hinging extension 106 reaching downwardly into a spacing 116 between the upper sleeve 105 and the lower mounting sleeve 104. The spacing 116 is sufficient to permit a flexing or bending of the light conductor portion between the sleeves when a push or pull is exerted on the hinging extension 106 by means of a push rod or pulling cable 107. When the manipulating means such as a push rod or pull cable 107 are operated, the light conducting fiber 103 with its enveloping jacket 102 is sufficiently bent in the portion extending through the spacing 116 so that the free end 114 of the light conductor fiber 103 may be bent or flexed in the direction of the arrow 115, whereby the laser radiation may be trained onto a tumor.

The sleeve 105 comprises the above mentioned bore 108 through which the free end 114 of the light conductor 103 extends with a close tolerance fit. Thus, a good mechanical connection is assured between the light conductor and the sleeve as well as a good heat transfer between these two elements. The sleeve 105 is further provided with a cavity 109 at its lower end into which the jacket 102 of the light conducting fiber 103 extends with a tight fit seating. The upper end of the bushing 105 is provided with a recess 110 thereby forming a concentric air gap 111 around the free end 114, whereby the free end 114 extends into said concentric air gap 111 and the upper edge of the sleeve 105 extends above the output end of the light conducting fiber 103. An improved light efficiency is achieved by means of radial apertures 112 as well as by means of a mirror reflecting coating 113 on the surface of the recess 110.

The described embodiment makes it possible to construct the apparatus in a slender shape. The expensive and trouble prone optical means for the deflection of the laser light beam have been substantially reduced. Further, an improved assurance of proper function is achieved due to the simple mechanical means for the bending which are not affected by the laser radiation so that higher laser energies may be employed for the intended purpose than was possible heretofore.

A good heat dissipation in the area of the output end of the light conducting fiber is achieved by making the sleeve 105 of a heat conducting metal such as copper, aluminum, or brass and the upper end or rather edge of the sleeve 105 should extend above the free end of the light conductor as mentioned.

The bending range of the light conducting fiber may be exactly established by the spacing 116 as shown in FIG. 6, and the lower sleeve 104 is preferably also made of a rigid material rigidly connected to the endoscopic viewing device 100.

Figure 2:
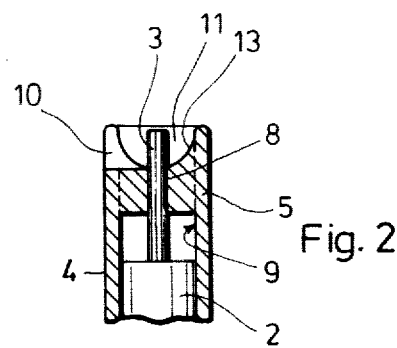
FIG. 2 shows on a somewhat enlarged scale and in an axial section the detail encircled by a dash-dotted line II in FIG. 1.

Referring to FIG. 1 the entire apparatus 1 for the endoscopic laser irradiation of human bladder tumors is arranged in a rigid pipe 20 in which there are operatively supported the conventional means of an endoscope. As in FIG. 6, the details of the endoscope are also not shown in FIG. 1 because they are part of the prior art. The bladder tumor is irradiated with the light emanating from a conventional laser, not shown in the drawings, and passing through a light conductor 3. The light conductor 3 is slidably guided in a pipe 4 at the lower end thereof and in a cavity 9 of a sleeve 5 at the upper end thereof. A hinge 6 operatively connects the metallic sleeve 5 to the upper end of the pipe 20. Contrary to the embodiment of FIG. 6, the free end of the light conductor 3 which constitutes the upper light output end is slidably received in the bore 8 of the sleeve 5 as best seen in FIG. 2. However, the tolerance between the free end of the light conductor where its jacket 2 has been removed, and the bore 8 of the sleeve 5 is sufficiently fine to assure the proper guiding. The free end of the light conductor 3 reaches into a ring gap 11 in a recess 10 at the upper end of the sleeve 5. Preferably, the recess 10 or rather its surface is coated with a mirror reflecting coating 13 as described above with reference to FIG. 6. Similarly, the upper end of the sleeve 5 is also provided with one or several apertures 10.

When performing a laser irradiation the light conducting fiber 3 takes up the position inside the sleeve as shown in FIG. 2. In this position the free end of the light conducting fiber 3 is somewhat reset relative to the upper edge of the sleeve 5 whereby a soiling or contamination of the light output is substantially prevented because any component suspended in the liquid in the bladder cannot easily deposit on the inwardly caving surface of the recess 11. Further, as in FIG. 6, the metallic sleeve 5 of copper or the like makes sure that a good heat dissipation is provided around the free end of the light conducting fiber, whereby the so-called burn-in problems of the prior art are avoided because contaminating particles are not burned into the surface of the sleeve recess. Thus, a thermal overloading of the free end of the fiber 3 is prevented.

In order to adjust the precise position or pinpointing of the laser radiation on the point to be treated, there is provided a push rod system 7 by means of which the sleeve 5 may be tilted or hinged about the hinge 6 by rotating a hand wheel 27 which drives the push rod 7 by conventional means. If necessary, the light fiber 3 may additionally be axially displaced. For example, a push rod 7 or respectively operating pull rope means are eccentrically secured to the hand wheel 27 for a precise and reproducible adjustment of the sleeve 5, whereby a rapid back and forth movement of the sleeve 5 is possible for a rinsing of the light output end of the light conductor fiber 3 in the liquid present in the bladder.

A manipulating mechanism, including shifting means 14 for the longitudinal displacement of the light conducting fiber 3 makes it possible to extend the output end of the light fiber, if necessary beyond the upper edge of the sleeve 5 so that, for example, when the output end should be soiled, the latter may be immersed into the liquid present in the bladder. Thus, in combination with the above described features of shifting the sleeve 5, a further improved rinsing of the fiber end may be accomplished when the latter has been slightly soiled. Thus, a removal of the entire apparatus from the urinary tract is avoided in most instances, whereby the heretofore required reinsertion is also avoided.

Figure 3:
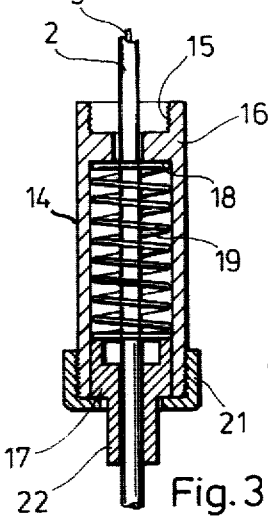
FIG. 3 is a longitudinal sectional view through a manipulating device as employed in the present apparatus.

The manipulating apparatus including the shifting device 14 for the light conducting fiber 3 is shown in the longitudinal, enlarged sectional view of FIG. 3 showing a housing type of bushing 16 provided with an inner threading 15 for securing the housing 16 to an extension nipple 14' shown in FIG. 1. The light conducting fiber 3 with its jacket 2 extends axially through the housing 16. The fiber 3 with its jacket is rigidly secured, for example, by conventional adhesive means to a glide bearing 17 which is guided in the housing 16 against the force of a spring 19 which is inserted between the slide bearing 17 and a shoulder 18 in the housing 16. The slide bearing 17 is in turn held in the housing 16 by a cap nut 21. In the shown position the fiber 3 with its jacket 2 takes up a starting position in which the outer end is retracted to the largest possible extent.

In operation, when the output end of the light conducting fiber 3 is to be displaced, pressure may be applied to the neck portion 22 of the slide bearing 17 or to an outward portion of the light conductor 3. In both instances the latter will be displaced against the force of the spring 19, whereby the slide bearing 17 moves upwardly because it is rigidly secured to the light conductor 3, whereby the upper, light output end of the conductor 3 may be extended out of the sleeve 5 into the free space of the bladder. Such displacement may be viewed by the endoscopic device 100 shown in FIG. 6.

Figure 4:
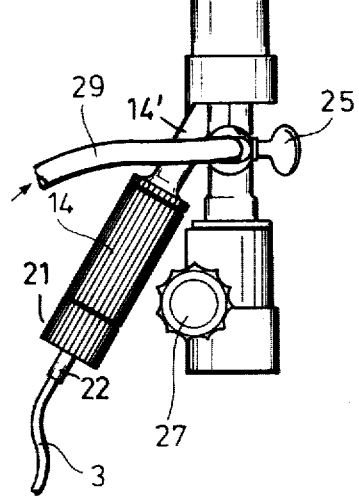
FIG. 4 is a sectional view axially through part of the lower inlet portion of the apparatus for illustrating the conduits for a rinsing fluid.
Figure 4:
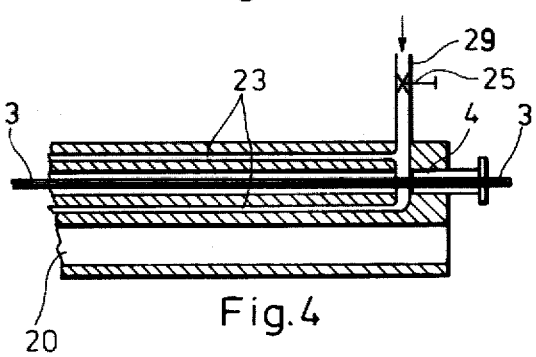

The described features may be further improved with regard to the rinsing efficiency by the means illustrated in FIG. 4 showing a device for producing a constant fluid pressure inside the bladder, for example, by means of a rinsing liquid. This device comprises hose means 23 for supplying the rinsing liquid into the bladder. These hose means 23 have an upper end 23' which reaches close to the output end of the fiber 3 to provide a whirling or eddy zone 30 so that the free end of the light conductor 3 is located in said eddy or whirling zone of the supplied rinsing liquid. The rinsing liquid may be supplied through a hose conduit 29 connected to the hose or conduit means 23 through a valve 25 at the operating end of the apparatus 1.

Figure 5:
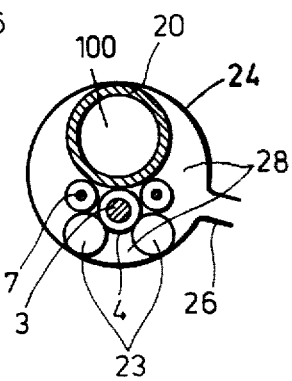
FIG. 5 is a sectional view along section line 5—5 in FIG. 1.

The rinsing liquid is returned to a further pipe 24 which may constitute an envelope for the entire structure as shown in FIGS. 1 and 5. The pipe or envelope 24 forms hollow spaces 28 which may receive the endoscopic device 100 shown in FIG. 6, whereby the endoscopic device 100 would be inserted into the tube or pipe 20. The light conductor 3 with its holding sleeve 4 and the rinsing hose means or conduits 23 are all operatively held in the envelope 24. The envelope 24 is also provided with a discharge port 26 near the operating end of the apparatus for the removal of any fluid or rinsing liquid from the bladder. The rinsing operation may be performed in an intermittent manner by opening and closing the valve 25 as desired at respective time intervals. In view of the above description, especially with reference to FIGS. 1 and 4 it will be appreciated that it is essential for an efficient rinsing operation to place the upper ends 23' of the hose or conduit means 23 close enough to the output end of the light conducting fiber 3 so that the latter will be located in the whirling or eddy zone 30 indicated by a dashed line in FIG. 1. The envelope 24 is open at its upper end.

Due to the movability of the sleeve 5 and of the light conductor 3 it is possible to keep the endoscopic apparatus inside the patient because it is now possible to keep the output end of the light conductor 3 free of contaminations by cleaning said free end in the liquid present in the bladder. The free end of the conductor 3 may be cleaned by a combination of two motions, once by moving the sleeve back and forth, whereby the light conductor is moved accordingly, or by moving the light conductor axially back and forth relative to the sleeve. Simultaneously, it is possible to maintain a constant pressure during the entire operation by means of the rinsing liquid. The formation of an eddy adjacent to the output end of the light conductor especially when the valve 25 is repeatedly opened and closed further increases the cleaning efficiency. The above mentioned maintaining of a constant pressure in the bladder has the further advantage that bladder distentions beyond a permissible range are avoided. This has the further advantage that the bladder wall is not likely to be perforated by the laser beam.

Although the invention has been described with reference to specific example embodiments, it will be appreciated, that it is intended to cover all modifications and equivalents within the scope of the appended claims.

What is claimed is:

1. An endoscopic bladder tumor treating apparatus using a laser radiation for said treating, comprising optical fiber light conductor means having an input end and an output end for transmitting a tumor treating laser radiation through said optical fiber light conductor means, endoscopic viewing means operatively arranged in parallel to said optical fiber light conductor means for inspecting an interior bladder wall, rigid sleeve means (5) operatively secured to said output end of said laser radiation transmitting optical fiber light conductor means for protecting said output end of the laser radiation transmitting optical fiber light conductor means against destruction by said tumor treating laser radiation, hinging means operatively secured to said rigid sleeve means, and manipulating means extending from said input end operatively connected to said hinging means for manipulating said output end substantially from said input end, said apparatus further comprising support means for slidably supporting said laser radiation transmitting optical fiber light conducting means in said rigid sleeve for axial displacement in said rigid sleeve means, shifting means operatively connected to said laser radiation transmitting optical fiber light conductor means, said shifting means being arranged adjacent said input end of said laser radiation transmitting optical fiber light conductor means, protective jacket means (2) operatively enclosing said laser radiation transmitting optical fiber light conductor means (3) except for said output end held by said rigid sleeve (5), said shifting means comprising slide bearing means (17), said light conductor means (3) with its jacket means (2) being operatively secured to said slide bearing means (17), said shifting means further comprising housing means (16, 21) holding said slide bearing means and spring means (19) also held in said housing means for biasing said slide bearing means into a starting position, said shifting means being operable to adjust said output end of said laser radiation transmitting optical fiber light conductor means (3) into a tumor treatment position whereby said output end is substantially recessed in said rigid sleeve (5) and into an output end cleaning position wherein said output end protrudes from said rigid sleeve (5).

2. The apparatus of claim 1, further comprising a cavity in said sleeve means (5), said jacket means (2) fitting into said cavity of said sleeve means, a bore extending through said sleeve means, said laser radiation transmitting optical fiber light conductor means having its jacket means removed along a length adjacent to said light conductor output end, said length of light conductor extending with a close tolerance fit through said bore in said sleeve means, said sleeve means further comprising a recess opposite said cavity, said light conductor output end extending into said recess whereby an air gap is formed between said sleeve means and said light conductor output end.

3. The apparatus of claim 2, wherein said sleeve means comprise aperture means extending radially outwardly from said recess substantially adjacent said output end of said light conductor means.

4. The apparatus of claim 2 or 3, further comprising a mirror reflecting coating applied to said recess in said sleeve means.

5. The apparatus of claim 1, wherein said sleeve means are made of metal and so located, that the sleeve means extend axially outside said endoscopic viewing means and afford good heat dissipation from the output end of said light conductor means thereby avoiding burn-in problems and thermal overload.

6. The apparatus of claim 1, comprising further sleeve means (104) operatively surrounding said jacket means (2) with a spacing (116) between said first mentioned sleeve means (5; 105) and said further sleeve means (104), said endoscopic viewing means comprising housing means rigidly connected to said further sleeve means.

7. The apparatus of claim 6, wherein said further sleeve means are made of a rigid material, said hinging means being located in said spacing between said first mentioned sleeve means and said further, rigid sleeve means and wherein said manipulating means comprise pull cable means extending from said hinging means to said input end and further comprising hand wheel means located at said input end and operatively coupled to said pull cable means for moving said rigid sleeve means laterally in different directions.

8. The apparatus of claim 1, further comprising hose means including a discharge opening operatively arranged to open adjacent said output end of said light conductor means for introducing a fluid into the bladder, said light conductor output end being located in an eddy or whirling zone of said fluid discharge opening.

9. The apparatus of claim 8, wherein said hose means are adapted for introducing a rinsing liquid into the bladder, said rinsing liquid forming said eddy or whirling zone.

10. The apparatus of claim 8, further comprising fluid supply means, and valve means operatively connecting said hose means to said fluid supply means, said apparatus further comprising outer tubular means (24) enclosing said light conductor means said endoscopic viewing means and said hose means, said outer tubular means providing hollow spaces for the removal of said fluid from the bladder.

* * * * *